(12) United States Patent
Yans (10) Patent No.: US 10,098,337 B2
(45) Date of Patent: Oct. 16, 2018

(54) MODULAR INSECT TRAP

(71) Applicant: Matthew W. Yans, Jacksonville, FL (US)

(72) Inventor: Matthew W. Yans, Jacksonville, FL (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 251 days.

(21) Appl. No.: 14/844,170

(22) Filed: Sep. 3, 2015

(65) Prior Publication Data

US 2016/0066555 A1 Mar. 10, 2016

Related U.S. Application Data (60) Provisional application No. 62/045,801, filed on Sep. 4, 2014.

(51) Int. Cl.
*A01M 1/02* (2006.01)
*A01M 1/10* (2006.01)
*A01M 1/14* (2006.01)
*A01N 59/04* (2006.01)

(52) U.S. Cl.
CPC ............... *A01M 1/14* (2013.01); *A01M 1/02* (2013.01); *A01M 1/023* (2013.01); *A01N 59/04* (2013.01); *Y02A 50/375* (2018.01)

(58) Field of Classification Search
CPC .......... A01M 1/00; A01M 1/02; A01M 1/023; A01M 1/14
USPC ..................................................... 43/107, 114
See application file for complete search history.

(56) References Cited

U.S. PATENT DOCUMENTS

| | | | | |
|---|---|---|---|---|
| 600,530 A | * | 3/1898 | Harig ..................... | A01M 1/14 43/115 |
| 790,620 A | * | 5/1905 | Crofford ................. | A01M 1/02 43/115 |
| 2,340,256 A | * | 1/1944 | Weil ....................... | A01M 1/14 43/131 |
| 4,031,654 A | * | 6/1977 | Gray ....................... | A01M 1/02 43/114 |

(Continued)

FOREIGN PATENT DOCUMENTS

CN 2265071 Y 10/1997

OTHER PUBLICATIONS

International Search Report and Written Opinion for PCT/US2015/046268, dated Dec. 3, 2015.

(Continued)

*Primary Examiner* — Darren W Ark
(74) *Attorney, Agent, or Firm* — Diane P. Tso; Ning Yang; Albert M. Churilla (57) ABSTRACT

The invention relates to a trap for collecting arthropods, for example ticks. The device comprises an attractant placed over an adhesive surface with the adhesive facing down or at an angle to prevent debris from inadvertently collecting. The arthropods, attracted to the device by the attractant then adhere to the adhesive surface on their dorsal side. The invention also relates to a method of using the device to collect insects by placing one or more of the devices in a desired collection area and collecting insects over a period of time without the need for constant monitoring of the devices.

15 Claims, 5 Drawing Sheets

(56) References Cited

U.S. PATENT DOCUMENTS

| | | | | |
|---|---|---|---|---|
| 4,217,722 | A * | 8/1980 | McMullen | A01M 1/14 43/114 |
| 5,042,194 | A * | 8/1991 | Cohen | A01M 1/2011 43/107 |
| 5,189,830 | A * | 3/1993 | Montemurro | A01M 1/023 43/107 |
| 6,530,172 | B2 * | 3/2003 | Lenz | A01M 1/023 43/112 |
| 6,920,716 | B2 * | 7/2005 | Kollars, Jr. | A01M 1/023 43/107 |
| 6,928,769 | B2 * | 8/2005 | Crawley | A01M 1/023 43/107 |
| 7,171,778 | B1 * | 2/2007 | Thompson, III | A01M 1/14 43/107 |
| 7,234,268 | B2 * | 6/2007 | Welch | A01M 1/02 43/112 |
| 8,402,690 | B2 * | 3/2013 | Schneidmiller | A01M 1/023 43/121 |
| 8,479,438 | B1 * | 7/2013 | Wilhelmi | A01M 1/106 43/121 |
| 8,635,807 | B2 * | 1/2014 | Frisch | A01M 1/023 43/114 |
| 9,565,846 | B2 * | 2/2017 | Vasudeva | A01M 1/023 |
| 9,686,973 | B2 * | 6/2017 | Nolen | A01M 1/023 |
| 2001/0001353 | A1 * | 5/2001 | Jones | A01M 1/14 43/114 |
| 2005/0210735 | A1 * | 9/2005 | Harmer | A01M 1/02 43/107 |
| 2006/0016120 | A1 * | 1/2006 | Masters | A01M 1/023 43/114 |
| 2011/0072712 | A1 * | 3/2011 | Black | A01M 1/02 43/123 |
| 2011/0203159 | A1 * | 8/2011 | McKnight | A01M 1/023 43/123 |
| 2012/0124888 | A1 * | 5/2012 | Lemberg | A01M 1/14 43/107 |
| 2012/0246998 | A1 * | 10/2012 | Vasudeva | A01M 1/023 43/114 |
| 2012/0285076 | A1 * | 11/2012 | Banfield | A01M 1/026 43/123 |
| 2012/0291336 | A1 * | 11/2012 | Friend | A01M 1/14 43/114 |
| 2013/0047495 | A1 * | 2/2013 | Frisch | A01M 1/10 43/114 |
| 2013/0067796 | A1 * | 3/2013 | Dong | A01M 1/14 43/109 |
| 2013/0142753 | A1 * | 6/2013 | Prohaska | A01N 59/04 424/84 |
| 2013/0291427 | A1 * | 11/2013 | Prohaska | A01M 1/023 43/107 |
| 2014/0033597 | A1 * | 2/2014 | Vasudeva | A01M 1/023 43/2 |
| 2015/0068105 | A1 * | 3/2015 | Vasudeva | A01M 1/023 43/114 |

OTHER PUBLICATIONS

Development of a Vector Arthropod (Tick and Flea) Pitfall or Sticky Trap with CO2 Attractant, Defense Health Program Solicitation, Apr. 24, 2013.
Hofmeester et al. Parasites & Vectors (2017) 10:433.
Ruilson, et al. Journal of Vector Ecology Jun. 2013:vol. 38, Issue 1, pp. 163-167 (abstract).
Mays, S.E., "Trapping Methods for Ixodid Ticks and Pathogen Associations of Amblyomma maculatum (Gulf Coast Tick) in Western Tennessee" Master's Thesis, University of Tennesee, 2015.
Gerhman et al. Parasites &Vectors 2012, 5:125.
Kensinger, B.J. and Allan, B. F., J. Med. Entomol. 48(3):708-711 (2011).
Armed Forces Pest Management Board Technical Guide No. 2006, Tick-Borne Diseases: Vector Surveillance and Control, Nov. 2012.
Borchert et al. J. Med. Entomol. 49(1) 210-214 (2012).
Miles, J., J. Med. Ent. vol. 5, No. 4: 491-495, Oct. 30, 1968.
Nevill, E. M., Onderstepoort J Vet. Res. (1964), 31(1). 59-66.
Garcia, R. (1962) Annals of the Entomological Society of America, 55(5). 605-606.

* cited by examiner

MODULAR INSECT TRAP

CROSS-REFERENCE TO RELATED APPLICATIONS

This application claims priority to U.S. provisional application 62/045,801, filed Sep. 4, 2014, which is hereby incorporated by reference.

BACKGROUND OF INVENTION

Field of Invention

The inventive subject matter relates to a device for collecting arthropods, including, but not limited to, ticks. The subject matter relates to a device for collecting arthropods that is simple to use and that does not require constant monitoring and a method of using the device.

Background Art

The ability to collect various arthropods ticks for study and/or analysis of populations is important for control nuisance of insects. Also, since many diseases are transmitted by zoonotic bacterial or viral reservoirs by arthropods, such as ticks and mosquitoes, the ability to control these pests are of public health concern.

Many methods for collection of ticks exist, such as "tick dragging", where a white cloth is dragged through terrain suspected of harboring ticks. Oher methods include swabbing suspected tick burrows using alcohol moistened swabs. Other methods include attracting the ticks to a collection area using attractants, typically $CO_2$, often in the form of dry ice. However, these methods are limited in their efficiency and often require significant man-hours to monitor and collect the ticks as they are attracted to the trap area.

SUMMARY OF THE INVENTION

The inventive device and method utilizes a trap system that attracts arthropods, such as ticks, to a collection area. In one embodiment, the device traps the arthropods, for example ants, stink bugs and ticks for collection at a later time. In this embodiment, arthropods are trapped by an adhesive coated surface, such as on adhesive tape. In one embodiment, the device enables the capture side, or side containing the adhesive, placed facing toward the ground or away from debris, but still suspended off the ground. Arthropods are directed toward the tape by an attractant whereby the insects are stuck to the adhesive surface on their dorsal side. In one embodiment, the trap permits collection of arthropods, such as ticks, over a period of time without debris collecting onto the adhesive tape since the adhesive side of the tape is facing down with no adhesive on the opposite side, which is facing upwards.

The inventive device can be used in a method for collecting arthropods, for example ticks. In the inventive method, one or more inventive devices are placed in a collection area or in multiple areas. Arthropods, such as ticks, are then collected over a period of time by simply removing the ticks adhered to the tape by their dorsal region.

In another embodiment, the device may use different attractants, depending on the intended insects to be trapped. In other embodiments, the adhesive surface may be oriented to maximally trap insects, such as facing the adhesive towards the walls of the attractant container rather than towards the ground. Crawling arthropods, such as ants, beetles, or ticks, or flying insects, such as stink bugs, may be induced to crawl up the container walls, where they become entrapped on their dorsal side by the adhesive surface surrounding the container.

DETAILED DESCRIPTION OF PREFERRED EMBODIMENTS

As used, herein, "arthropod" includes all insect species, as well as non-insect arthropods, such as spiders, centipedes, etc., whether flying or non-flying. Use of the term "insect" throughout is not intended to limit the use of the device to other non-insect arthropod species. As used herein, the terms "arthropod" and "insect" can be used interchangeably and should in all cases be understood using broadest definition of the term "arthropod."

Adhesive-based traps may be used to lessen the labor requirements, but many arthropods, such as ticks, ants and stink bugs, are strong enough to crawl across an adhesive-coated surface without getting stuck. Additionally, upwards facing adhesive surfaces capture large numbers of non-target insects and other non-living debris, such as dust and plant matter. To address this problem, the device described herein comprises an adhesive surface with the adhesive facing down or away from any potential debris. Although the embodiments described herein are primarily focused on ticks as an example, it should be easily understood by one of ordinary skill in the art that the device may be modified to efficiently capture any desired arthropod, while remaining within the scope of the present invention.

The inventive device utilizes a trap system that attracts arthropods, including, as examples, but not limited to ants, stink bugs, and ticks, to a collection area. In one embodiment, the device traps the insects for collection at a later time. In this embodiment, arthropods are trapped by an adhesive coated surface, such as on tape or strip. In a further embodiment, the adhesive coated surface is only on one side of the tape, such as adhesive tape, with the opposite side not containing adhesive. In one embodiment, the device enables the adhesive tape to be placed with the adhesive angled or facing down, such as toward the ground, but still suspended off the ground. The placement of the adhesive tape traps the insects by adhering to their dorsal side. A feature of the inventive device is that the device enables the passive collection of arthropods without damaging them for later collection. Another feature is that insects can be collected over a period of time without the need for constant monitoring and without debris collecting on the adhesive surface, since it is facing down, which would impede the efficiency of collection.

Example 1

Figure 1:
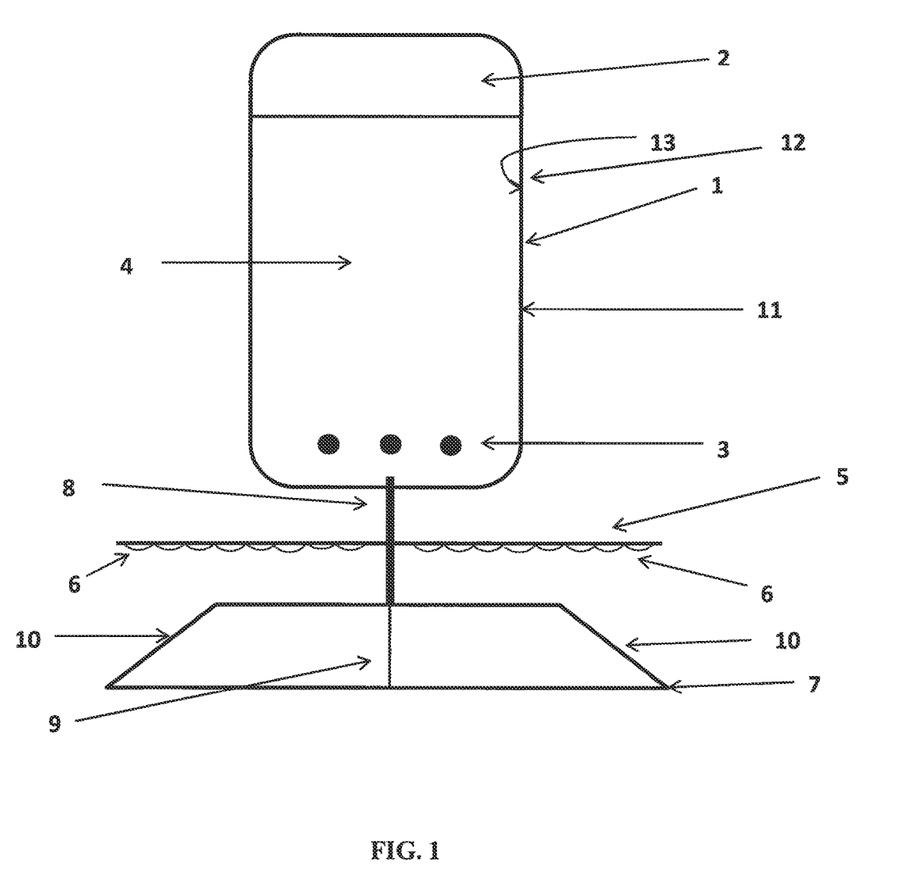
FIG. 1. Side view of one example configuration illustrating beveled base and placement of the adhesive strip relative to the base.

The device, illustrated in FIG. 1, comprises a container 1, with at least one wall 11, comprising an outside 12, and inside 13, surface; and an adhesive tape or strip 5, for example adhesive tape, with the adhesive side 6 facing down. In another embodiment, the device further comprises a base 7 for supporting the container 1. In one embodiment, not illustrated herein, the adhesive tape or strip 5 may additionally be provided with a covering or backing over the adhesive 6, which may then be removed when trapping is desired to commence. In another embodiment, double-sided tape can be used but with backing on one side not removed. In another embodiment, the container 1 is placed directly on the base 7 with the weight of the container 1 and its contents, such as attractant 4, holding the container 1 in place. In another embodiment, as illustrated in FIG. 1, the container 1 can be secured to the base 7 by an attachment means. As an example, the container 1 can simply rest on the base 7 or can be secured to the base, such as, for example, with adhesive tape or via a post 8 attached to the base 7 or other attachments or connections between the base 7 and the container 1. In one embodiment, the post 8 fits through a hole in the container 1 to easily secure the container 1 to the base 7. The base 7 comprises a beveled face 10 with a negative slope or angle toward the bottom of the base 7. Typically, the slope or angle of the beveled face 10 is approximately 45° with respect to the bottom of the base 7, but may be between 0° and 90°. In another embodiment, the adhesive tape or strip 5 is placed under the container 1 or around the container 1 with the adhesive side down 6 facing down and overlaying, but not touching, the beveled face 10 of the base 7. The adhesive tape or strip 5 is placed generally parallel to the bottom of the base 7 such that when an arthropod, such as a tick, crawls up the beveled face 10 it is induced to approach closer to the adhesive side 6 until it becomes stuck to the adhesive 6 on its dorsal side. In one embodiment, the base 7 is additionally capable of being folded or taken apart via a hinge or break-point 9 for easy storage and set-up.

The container 1 can be any of a number of sizes, from ½ to 2 gallons, with a typical size of 1 gallon, and comprises one or more holes 3, penetrating both the outside 12 and inside 13 surfaces of the wall 11 near the bottom of the container 1. The holes 3, which are placed to best attract insects given a specific capture situation, are, in one embodiment, ½ to 2 inches from the base of container 1. In a typical embodiment, they are 1½ inches from the base of the container 1. The size of the hole(s) 3 permits the escape of $CO_2$, or other attractant, from the container 1. Typically the holes 3 are of an inch, with a typical size of 5/16 of an inch in diameter. As an illustration, FIG. 1 shows a device with three holes 3. The container 1 further comprises a top 2 to seal or fill the container 1, can be made of any substance including, but not limited to metal or plastic.

Figure 2:
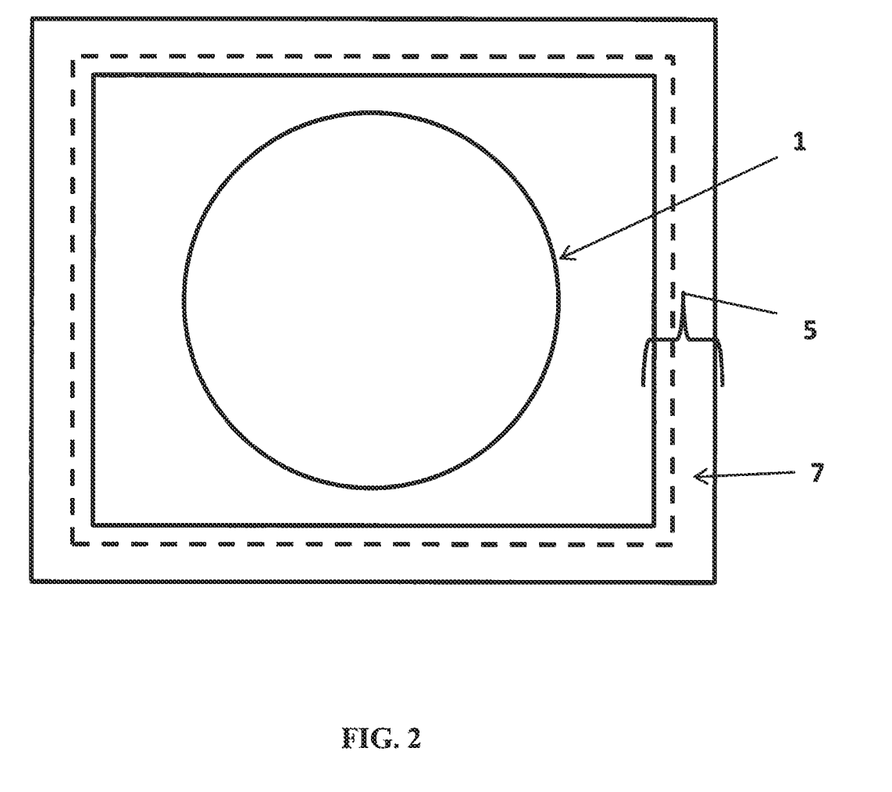
FIG. 2. Top view of trap device illustrating placement of attractant container onto the beveled base.

This structural relationship of the container and the base and tape is further illustrated in FIG. 2. As illustrated in FIG. 2, in one embodiment a significant portion (50% to 100%) of the beveled face 10 is canopied by the adhesive tape 5 with the adhesive side 6 facing, but not touching, the beveled portion 10 of the base 7.

Although other arthropod attractants are envisioned, in one embodiment, dry ice, which upon warming emits $CO_2$, is used. Dry ice or another attractant 4 is placed inside the container 1. The container 1 is large enough to contain adequate attractant 4 for the device to operate over an extended period, including one or more days.

Figure 3:
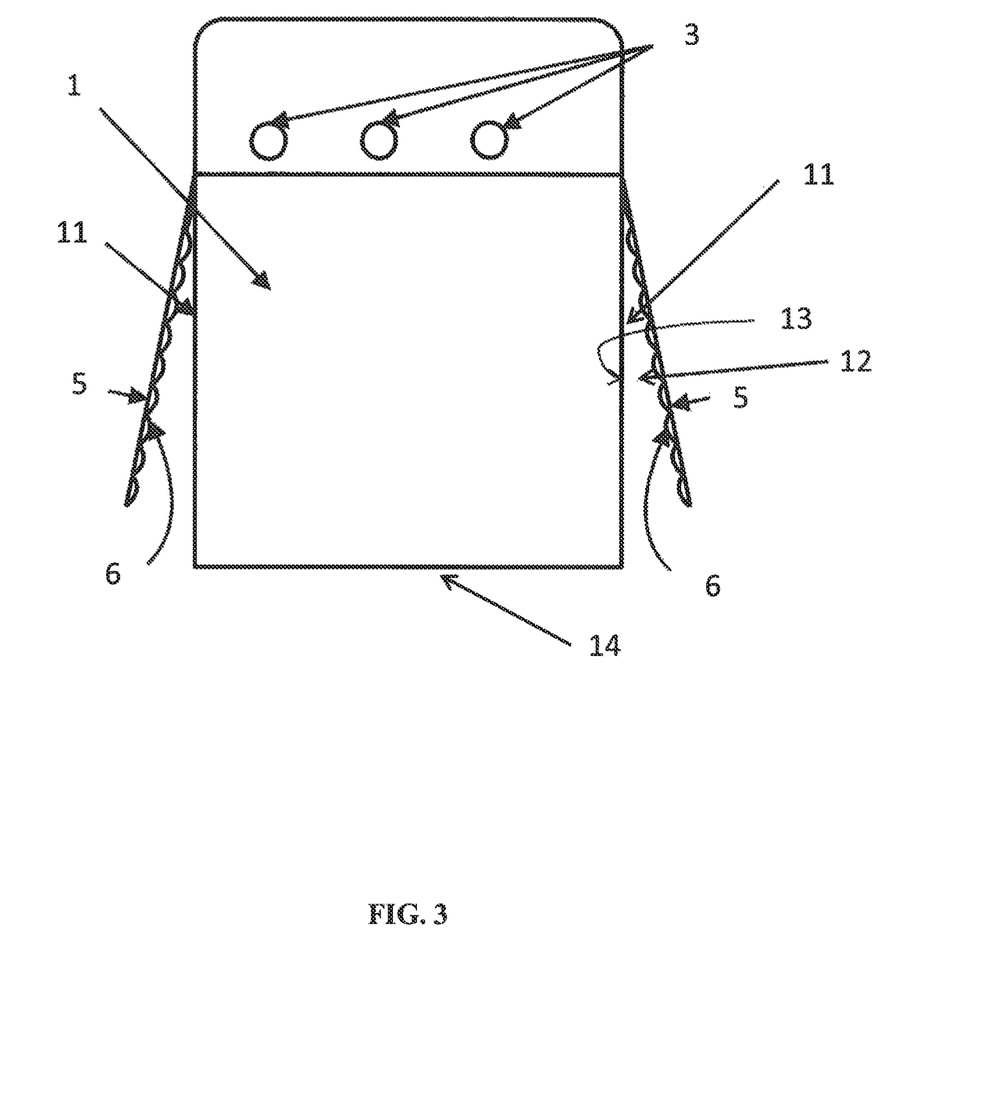
FIG. 3. Side view of second example configuration, wherein the container and beveled base may be a incorporated into a single integrated piece.

Another embodiment is illustrated in FIG. 3. In this embodiment, the container 1 is merged with the base into a single unit. The container comprises at least one wall 11, with outside 12 and inside 13 surfaces. Arthropods are capable of crawling up the outside surface 12. The adhesive tape or strip 5 is placed around the container 1 such that the adhesive face 6 is facing towards the outside surface 12 of the at least one wall 11 and is attached at one end to the container 1 such that the adhesive face 6 and the wall 11 form an angle between 0° and 90°. In one embodiment, that angle is 45°. In this embodiment, the container is placed with its bottom side 14 on the ground. Holes 3 are placed in the side of the container 1 above the adhesive tape 5, such that crawling arthropods must first crawl up the wall 11 and subsequently get stuck on the adhesive face 6 in their attempt to reach the attractant.

Figure 4:
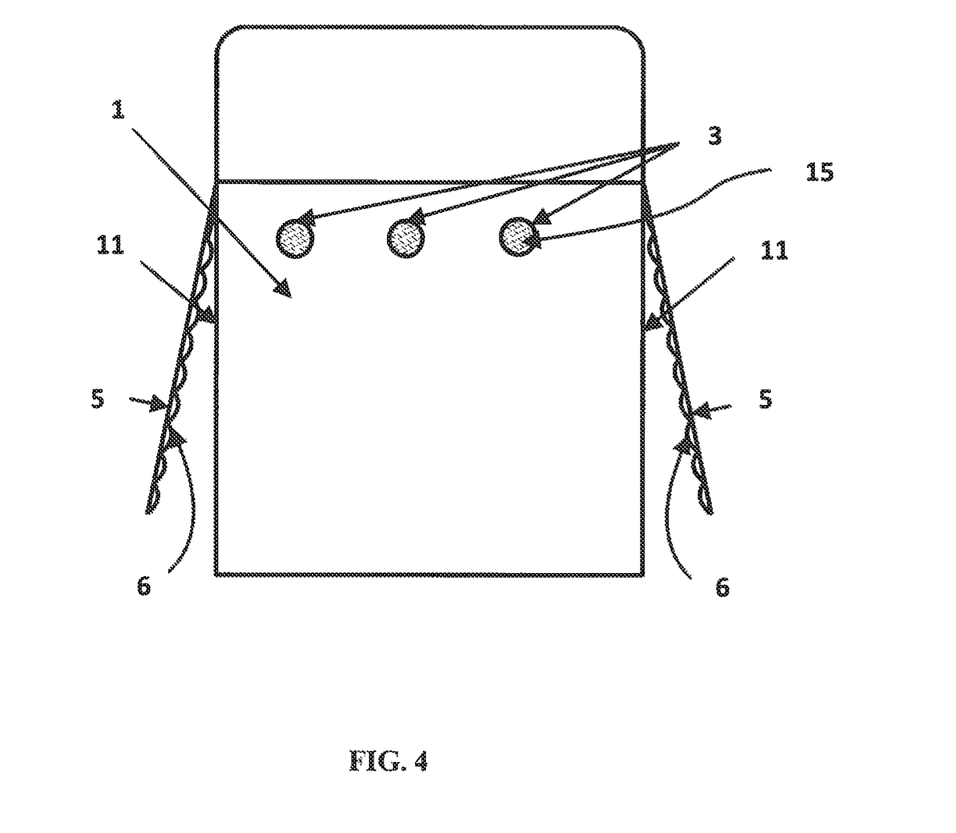
FIG. 4. Side view of third example configuration, wherein the container and the base are integrated into a single piece and with the holes for the attractant source screened so as to prevent entry by the target arthropod.

FIG. 4 depicts another embodiment of the invention that is suitable for both flying and crawling insects. In this embodiment, the at least one hole 3, penetrating the outside 12 and inside 13 surface of the at least one wall 11 of the container 1, are located below the point at which the adhesive tape or strip 5 attaches to the wall 11. In this embodiment, the at least one holes 3 are not visible from exterior of the trap. In this embodiment, or any of the above embodiments, the holes 3 may be smaller than ¼ of an inch in diameter to prevent ingress by arthropods into the container 1. Alternately, the holes 3 may be covered by a mesh 15 which is fine enough to exclude arthropods and yet large enough for attractive amounts of the attractant to be released. In the embodiment depicted in FIG. 4, flying or crawling arthropods are drawn towards and through the progressively narrowing gap between the wall 11 and the adhesive face 6 until they become stuck on the adhesive face 6 by their ventral or, preferably, dorsal parts. This embodiment does not require placement on the ground and may be hung or otherwise suspended above the ground, as there is no way for the target arthropods to reach the source of attractant without contacting the adhesive face 6 and subsequently becoming stuck.

Example 2: Method for Trapping Arthropods

The device, such as the embodiments described in Example 1, can be used in a method for trapping arthropods without the need for constant monitoring of the devices. In one embodiment, the method comprises placing the device described in Example 1 in a desired collection area. It may be necessary to trim vegetation so the device sits firmly on the ground. If the device is the embodiment as illustrated in FIG. 1, the container 1 is then placed on and optionally secured to the base 7, by either adhesive tape or other connecting means, such as via a post and hole arrangement 8 as illustrated in FIG. 1. An adhesive tape or strip 5, such as adhesive tape, with the adhesive side 6 covered by an optional backing, can be utilized such that when the backing is removed the adhesive face 6 will face down toward the beveling 10 of the base 7. An insect attractant is placed into the container 1. In one embodiment, the attractant is a $CO_2$ source such as dry ice, which would be useful for collection of arthropods such as ticks. However, other attractants are envisioned to be able to be utilized depending on factors, such as the arthropod to be collected and collection area.

The device is left in place until enough attractant is emitting through the holes 3 (see FIGS. 1-4). After an adequate period of time, the backing on the adhesive tape or strip 5 is removed to expose the adhesive face 6. Ticks are periodically removed from the tape, which are adhered via their dorsal region. In one embodiment, one or more devices can be set up within an area. Monitoring of the device can be multiple times in a single day, daily or longer.

Example 3: Comparison of Collection Methods

The effectiveness of the inventive method was compared to two other, commonly utilized methods to collect ticks (*Amblyomma americanum*). The two methods included attraction and collection of insects on a white cloth and by dragging.

The three methods were compared side by side and conducted in late June/early July. Dragging was conducted using a double layer white denim cloth 1-square meter in size. The cloth was dragged 20 meters. This was repeated ten (10) times. Adjacent and while the dragging was ongoing, ticks were collected by a second "$CO_2$" method. In the "$CO_2$" method, ticks were collected onto 1 square meter white denim, double layer sheet. A cooler, similar to the container 1 described in Example 1, containing dry ice as a $CO_2$ source, was placed in the center of the sheet. Ten (10) replicates of the "$CO_2$" method were set 16 meters apart to collect simultaneously. Interspersed evenly between the "$CO_2$" collection replicates (i.e., 8 meters from each "$CO_2$" replicate), ticks were collected by the inventive method, using the set up as described in Example 1. Collection of ticks was carried out four (4) hours after set-up of $CO_2$ collection methods.

Figure 5:
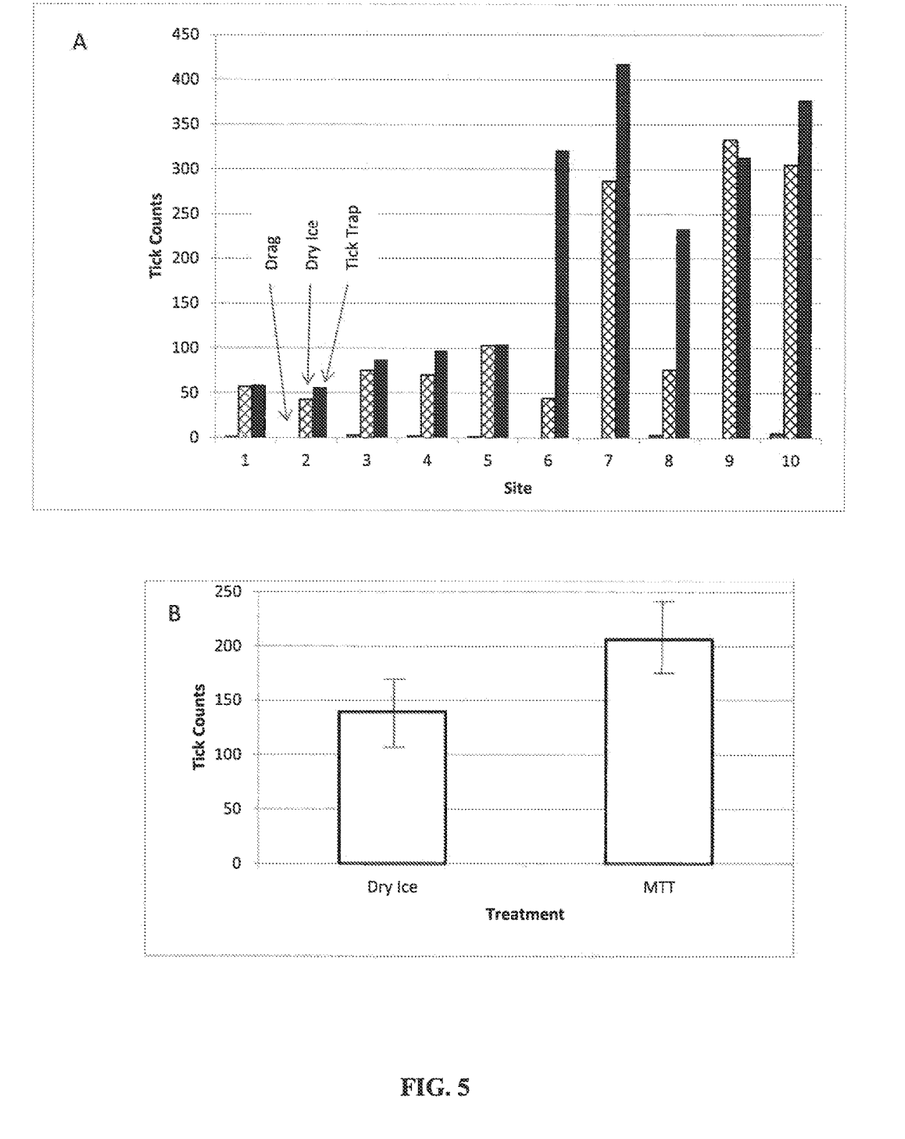
FIG. 5. Comparison of insect collection (i.e., ticks) by three methods; inventive method; dry ice onto denim, white cloth; dragging. The data for each method is as indicated by arrows for each collection replicate. Graph (A) represents total number of ticks collected each of ten (10) sites by the three methods. Graph (B) represents the mean counts from all the sites depicted in Graph (A).

The results of the studies are shown in FIG. 5. In FIG. 5(A) the number of ticks collected at each of the 10 sites by each of the methods is shown. FIG. 5(B) shows the mean of all sites for each of the methods. Since a high percentage of larvae collected could artificially skew the data, the number of different life-stages of ticks (*Amblyomma americanum*) was also evaluated in the collected tick population. It was found that the larva population constituted, over all the sites collected, only a small (i.e., less than 15%) of the total number of ticks collected. The remaining ticks were adult male/female and nymph populations.

The data in FIG. 5 clearly indicates that the "$CO_2$" method collection onto cloths and the inventive device were far superior to the standard dragging method. No more than 10 ticks were collected in any site using the dragging method, and several sites resulted in no ticks caught via dragging, whereas the other two methods collected between 45 and 425 ticks per site. Additionally, also illustrated in FIG. 5(B), the inventive device was superior to collection onto sheets using the same attractant. Furthermore, although in the study illustrated in Example 3 ticks were collected after fours (4) hours, the inventive method enables collection over longer periods of time, if desired, illustrating its greater flexibility, utility and convenience.

Although Example 3 illustrates the collection of ticks, similar collection results are anticipated for the collection of other insects.

Obviously, many modifications and variations of the present invention are possible, in light of the above teachings. It is therefore to be understood that, within the scope of the appended claims, the invention may be practiced other than as specifically described.

What is claimed is:

1. A device for collecting arthropods comprising:
   a. a container, which has at least one wall and at least one hole located in and penetrating said at least one wall;
   b. an arthropod attractant, which is contained within said container such that said arthropod attractant is released from said at least one hole located in and penetrating said at least one wall;
   c. an adhesive tape or strip, which comprises at least one adhesive surface, wherein said at least one adhesive surface is suspended off the ground, and wherein the adhesive tape or strip is placed on the device such that attracted crawling arthropods are directed towards the adhesive tape or strip whereby the attracted crawling arthropods are induced to approach the at least one adhesive surface on the device until they become adhered to the at least one adhesive surface on their dorsal side, wherein said device comprises a beveled base, wherein said beveled base comprises a beveled face and a substantially horizontal lower face, wherein said beveled face is oriented at an acute angle relative to the substantially horizontal lower face of the beveled base; and wherein the adhesive tape or strip is attached to a top of the beveled base parallel to the substantially horizontal lower face of the beveled base such that the adhesive tape or strip is over-lapping but not touching the beveled face, and wherein the at least one adhesive surface of the adhesive tape or strip faces towards the beveled face such that when said arthropods crawl up the beveled face of the beveled base they become entrapped on the dorsal sides by the at least one adhesive surface.

2. The device of claim 1, wherein the beveled face is 0° to 90° relative to the substantially horizontal lower face of the beveled base.

3. The device of claim 2 wherein the beveled face is approximately 45° relative to the substantially horizontal lower face of the beveled base.

4. The device of claim 1, wherein said adhesive tape or strip further comprises a backing over the at least one adhesive surface that can be removed prior to use of the device.

5. The device of claim 1, wherein said arthropods are selected from the group consisting of ants, beetles, stink bugs, and ticks.

6. The device of claim 5 wherein said arthropod are ticks.

7. The device of claim 1, wherein said arthropod attractant is a source of $CO_2$.

8. The device of claim 1, wherein said beveled base can be folded.

9. The device of claim 1, wherein said at least one hole is located ½ to 2 inches from a bottom of the container such that the arthropod attractant is released from said at least one hole.

10. The device of claim 1 wherein said container is secured to said beveled base.

11. The device of claim 10, wherein said container is secured to said beveled base by a post that connects the container to the beveled base.

12. The device of claim 1 wherein the adhesive tape or strip is over-lapping but not touching the beveled face such that 50% to 100% of the beveled face is canopied by the adhesive tape or strip.

13. A method of trapping arthropods comprising:
   a. placing one or more of the devices recited in any one of claims 1, 2, 4-5, 7-11, 6, 12 or 3 in a desired collection area;

b. removing trapped arthropods from said one or more of the devices at least once after said one or more of the devices are placed in the desired collection area.

14. The method of claim 13, wherein said arthropods are selected from the group consisting of ants, beetles, stink bugs, and ticks.

15. The method of claim 13, wherein said at least one hole restricts the arthropods from entering said at least one hole by means of diameter or mesh fine enough to exclude the arthropods yet large enough for attractive amounts of the attractant to be released.

* * * * *